United States Patent
Konno et al.

(10) Patent No.: US 11,364,091 B2
(45) Date of Patent: Jun. 21, 2022

(54) SENSOR SYSTEM

(71) Applicant: NIHON KOHDEN CORPORATION, Tokyo (JP)

(72) Inventors: Norihito Konno, Tokyo (JP); Hirohiko Ikeya, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 16 days.

(21) Appl. No.: 16/098,247

(22) PCT Filed: Jun. 13, 2017

(86) PCT No.: PCT/JP2017/021761
§ 371 (c)(1),
(2) Date: Nov. 1, 2018

(87) PCT Pub. No.: WO2018/003485
PCT Pub. Date: Jan. 4, 2018

(65) Prior Publication Data
US 2019/0142547 A1    May 16, 2019

(30) Foreign Application Priority Data
Jun. 28, 2016 (JP) .............................. JP2016-127894

(51) Int. Cl.
*A61B 5/00* (2006.01)
*A61B 90/98* (2016.01)
(Continued)

(52) U.S. Cl.
CPC .............. *A61B 90/98* (2016.02); *A61B 5/002* (2013.01); *A61B 5/0006* (2013.01);
(Continued)

(58) Field of Classification Search
CPC ....... A61B 90/98; A61B 5/0028; A61B 5/002; A61B 5/0006; A61B 5/0008;
(Continued)

(56) References Cited

U.S. PATENT DOCUMENTS

| 8,558,933 B2 | 10/2013 | Sakai | |
|---|---|---|---|
| 2009/0184842 A1* | 7/2009 | Baldus | G16H 40/63 340/870.07 |

(Continued)

FOREIGN PATENT DOCUMENTS

| JP | 2001-187611 A | 7/2001 |
|---|---|---|
| JP | 2006-202111 A | 8/2006 |

(Continued)

OTHER PUBLICATIONS

International Search Report issued in Patent Application No. PCT/JP2017/021761 dated Aug. 29, 2017.
Written Opinion issued in Patent Application No. PCT/JP2017/021761 dated Aug. 29, 2017.
(Continued)

*Primary Examiner* — Rex R Holmes
(74) *Attorney, Agent, or Firm* — Pearne & Gordon LLP

(57) ABSTRACT

A sensor system including: a wristband (2) which has a storage unit storing patient identification information so that a patient can be identified by the patient identification information; and a sensor (3) which can measure vital information of the patient; wherein: the wristband (2) can transmit the patient identification information to the sensor (3) by human body communication through a surface of a body of the patient in a state in which the wristband (2) and the sensor (3) are attached to the patient; and the sensor (3) associates the patient identification information with the
(Continued)

vital information and then transmits the vital information including the patient identification information to a bedside monitor 4.

6 Claims, 3 Drawing Sheets

(51) Int. Cl.
    *A61B 5/1455*     (2006.01)
    *A61B 5/08*     (2006.01)
    *A61B 5/318*     (2021.01)

(52) U.S. Cl.
    CPC .......... *A61B 5/0008* (2013.01); *A61B 5/0028* (2013.01); *A61B 5/0031* (2013.01); *A61B 5/681* (2013.01); *A61B 5/0816* (2013.01); *A61B 5/14551* (2013.01); *A61B 5/318* (2021.01); *A61B 2562/08* (2013.01)

(58) Field of Classification Search
    CPC .................. A61B 5/0031; A61B 5/681; A61B 5/14551; A61B 5/0402; A61B 5/0816; A61B 2562/08; G06F 19/3418; G16H 10/60; G16H 40/63; G16H 40/20
    See application file for complete search history.

(56) References Cited

U.S. PATENT DOCUMENTS

| | | | |
|---|---|---|---|
| 2011/0221590 A1 | 9/2011 | Baker et al. | |
| 2011/0263950 A1* | 10/2011 | Larson | G16H 20/00 |
| | | | 600/301 |
| 2012/0029313 A1* | 2/2012 | Burdett | A61B 5/1113 |
| | | | 600/301 |
| 2016/0335426 A1 | 11/2016 | Cherry et al. | |
| 2017/0111123 A1 | 4/2017 | Ouzounov | |

FOREIGN PATENT DOCUMENTS

| | | | | |
|---|---|---|---|---|
| JP | 2017-508225 A | 3/2017 | | |
| JP | 2017-522777 A | 8/2017 | | |
| WO | 2008-014432 A2 | 1/2008 | | |
| WO | WO-2008014432 A2 * | 1/2008 | .......... | A61B 5/0002 |
| WO | 2015-109360 A1 | 7/2015 | | |
| WO | 2015-180937 A1 | 12/2015 | | |

OTHER PUBLICATIONS

Japanese Office Action issued in Japanese Patent Application No. 2016-127894 dated May 7, 2020.

* cited by examiner

[Fig. 1]
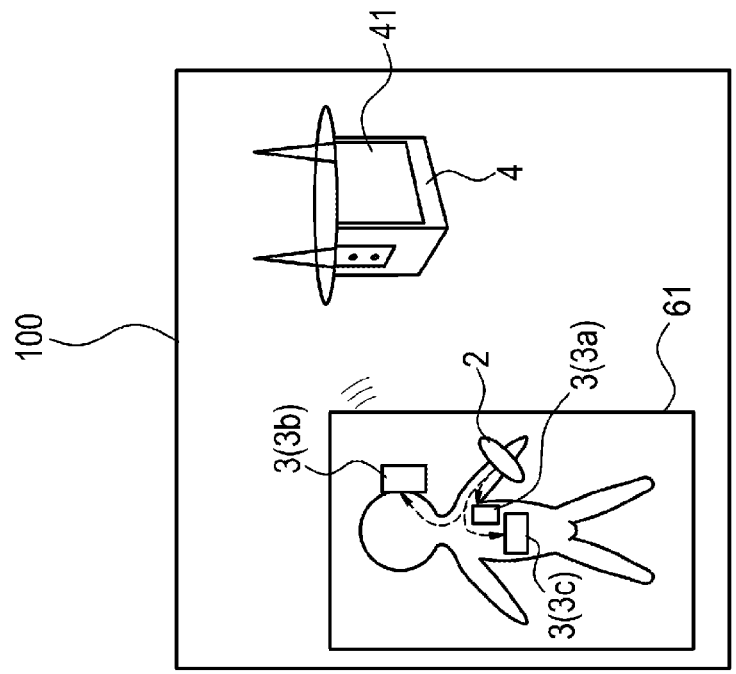
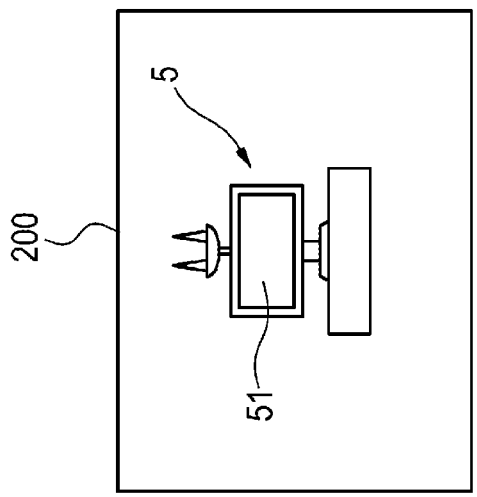

[Fig. 2]
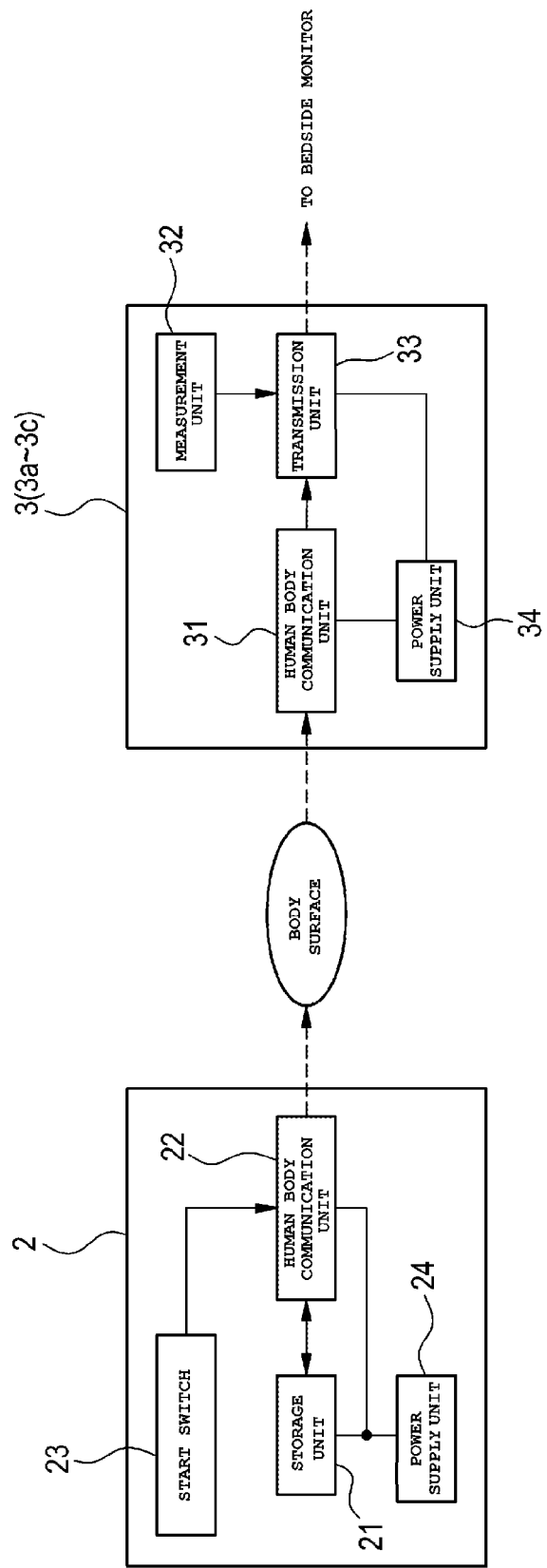

[Fig. 3]
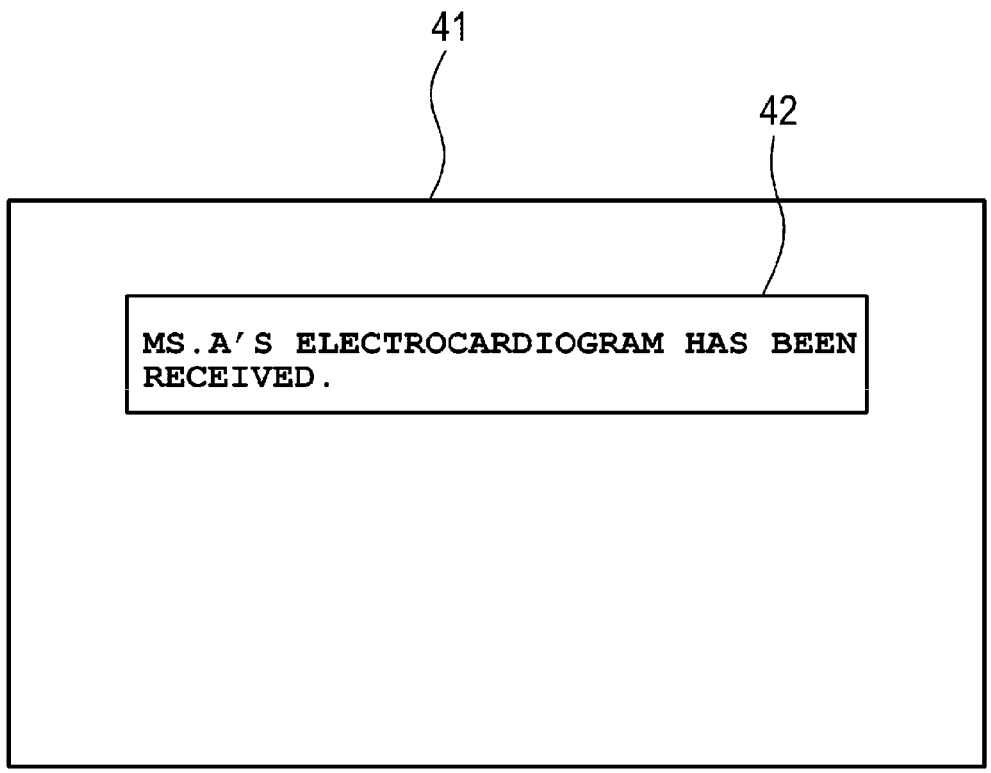
[Fig. 4]
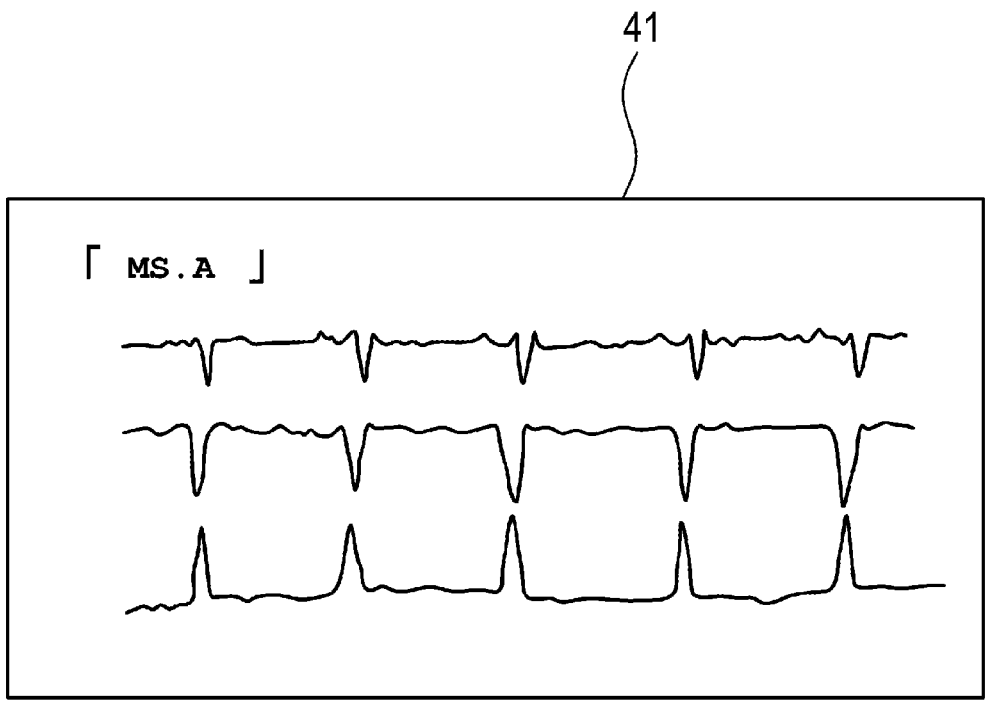

SENSOR SYSTEM

TECHNICAL FIELD

The present invention relates to a sensor system which acquires information by use of a sensor.

BACKGROUND ART

Assume that a sensor which is attached to a patient is connected to a display device by a cable (wire). In such a configuration, movement of the patent may be restricted by the cable. To solve this problem, for example, there is a system having a configuration in which a sensor can communicate with a display device by wireless (see Patent Literature 1).

CITATION LIST

Patent Literature

PTL 1: U.S. Pat. No. 8,558,933

SUMMARY OF INVENTION

Technical Problem

However, in the system according to Patent Literature 1, when a plurality of patients are at a short distance from the display device, wireless communication between one sensor and the display device may be crossed with wireless communication between another sensor and the display device. Thus, in an anticipated situation, pieces of vital information measured by the sensors cannot be associated with the patients accurately respectively.

To solve the problem, an object of the invention is to provide a sensor system in which vital information measured by a sensor and a patient can be associated with each other accurately.

Solution to Problem

In order to achieve the foregoing object, the invention provides a sensor system including: an ID tag which has a storage unit storing patient identification information so that a patient can be identified by the patient identification information; and a sensor which can measure vital information of the patient; wherein: the ID tag can transmit the patient identification information to the sensor by human body communication through a surface of a body of the patient in a state in which the ID tag and the sensor are attached to the patient; and the sensor associates the patient identification information with the vital information and then transmits the vital information including the patient identification information to an external device.

According to the configuration, patient identification information given uniquely to each patient by a medical worker is transmitted to the sensor through a body surface of the patient. Therefore, the sensor can surely associate the patient identification information of the patient on which the sensor is attached, with vital information of the patient. The vital information (a vital signal including the patient identification information) which has been linked with the patient identification information accurately can be received by the external device. Accordingly, the vital information (the vital signal including the patient identification information) can be displayed on a display screen etc. in a state in which the sensor measuring the vital information has been associated with the patient accurately.

According to the sensor system according to the invention, it is possible to associate the vital information measured by the sensor with the patient accurately.

BRIEF DESCRIPTION OF DRAWINGS

FIG. 1 A schematic view of a sensor system according to an embodiment of the invention.

FIG. 2 A block diagram for explaining functions of a wristband and a sensor.

FIG. 3 A view showing an example of a message image displayed on a bedside monitor.

FIG. 4 A view showing an example of vital information displayed on the bedside monitor.

DESCRIPTION OF EMBODIMENTS

An embodiment of the invention will be described below by way of example with reference to the drawings. As shown in FIG. 1, a sensor system 1 according to the embodiment is provided with a wristband 2 (an example of an ID tag. ID: identification) which is attached on each patient, sensors 3 which are likewise attached on the patient, a bedside monitor 4 (an example of an external device) which can communicate with the sensors 3, and a nurse call system 5 which can communicate with the bedside monitor 4. Incidentally, FIG. 1 shows a state of a portion of one floor in a hospital. The bedside monitor 4 is placed in a hospital room 100, and the nurse call system 5 is placed in a nurse station 200.

The wristband 2 can be attached on a part, such as a wrist or an ankle, of the body of the patient. Patient identification information is described in a visually confirmable form on the wristband 2 so that the patient can be identified by the patient identification information. The patient identification information is unique patient information which is given from the hospital to each patient. For example, the patient identification information may include a patient ID, a patient's name, a patient's registration card number, etc.

The sensors 3 are attached on parts of the body of the patient if necessary so that the sensors 3 can measure vital information of the patient. For example, the sensors 3 can include a sensor 3a for measuring an electrocardiogram, a sensor 3b for measuring body temperature or SpO$_2$, a sensor 3c for measuring respiration, etc. Each of the sensors 3 is a wireless sensor which has a short range wireless communication function and which is configured to be able to make wireless communicate (e.g. Bluetooth (registered trademark)) with the bedside monitor 4.

The bedside monitor 4 is placed for each bed used by a hospitalized patient. The bedside monitor 4 has a display screen 41 so that vital information of the patient received from the sensors 3 by wireless communication can be displayed on the display screen 41. In addition, the bedside monitor 4 is configured to be able to communicate with the nurse call system 5. The bedside monitor 4 and the nurse call system 5 can be connected to each other, for example, through a wired cable or a wireless LAN (LAN: Local Area Network).

A patient information table in which information about all hospitalized patients has been recorded is held by the nurse call system 5. For example, pieces of information including a patient ID, a patient's name, a patient's room number, a bed number, an attending doctor, an attending nurse, etc. are stored respectively in association with each patient in the patient information table. The nurse call system 5 can transmit the information of the patient information table to the bedside monitor 4 by wireless communication. In addition, the nurse call system 5 has a display screen 51 so that the vital information of the patient received from the bedside monitor 4 can be displayed on the display screen 51.

As shown in FIG. 2, the wristband 2 is provided with an electronic device portion constituted by a storage unit 21, a human body communication unit 22, a start switch 23, and a power supply unit 24. The patient identification information is stored in the storage unit 21. The stored patient identification information may be one kind of information or a plurality of kinds of information selected from the patient ID, the patient's name, the patient's registration card number, etc. The patient identification information of the storage unit 21 can be rewritten. The patient identification information can be rewritten into the electronic device portion so that the electronic device portion can be used repeatedly.

The human body communication unit 22 is a communication portion for performing human body communication with each of the sensors 3. For example, the human body communication unit 22 is constituted by an IC chip. The human body communication is a communication method in which a human body (dielectric) is used as a communication medium without using any cable. The human body communication is based on the international standard "IEEE 802.15.6". An electric field method is used in the human body communication. Communication in the electric field method is, for example, performed as follows. That is, a signal is given to an electrostatic layer on a body surface originally belonging to the human body serving as a dielectric. Incidentally, the surface of the human body is covered with the electrostatic layer several centimeters thick. Accordingly, the wristband 2 can communicate with the sensor 3 by the electric field method even in a state in which the human body communication unit 22 is not in direct contact with the human body but near the one.

The start switch 23 is a switch for activating the human body communication unit 22 to start human body communication. For example, a coil cell battery can be used as the power supply unit 24.

As shown in FIG. 2, the sensor 3 is provided with a human body communication unit 31, a measurement unit 32, a transmission unit 33, and a power supply unit 34. The human body communication unit 31 is a communication unit which has a similar function to the human body communication unit 22 of the aforementioned wristband 2. The human body communication unit 31 performs human body communication with the human body communication unit 22 of the wristband 2 to receive the patient identification information held by the wristband 2.

The measurement unit 32 measures vital information of the patient on which the sensor 3 is attached. The transmission unit 33 associates the patient identification information received from the wristband 2 with the vital information measured by the measurement unit 32, and transmits the vital information including the patient identification information to the bedside monitor 4. For example, a coin cell battery can be used as the power supply unit 34.

Next, an operation example of the sensor system 1 will be described with reference to FIGS. 1 to 4. First, as initial setting, a patient information table for a patient (e.g. called patient A) whose hospitalization has been determined is generated on the nurse call system 5. In addition, for example, the name (Ms. A) of the patient A is inscribed on the wristband 2, and a patient ID of the patient A is written into the storage unit 21 embedded in the wristband 2. The wristband 2 is delivered from a medical worker to the patient A, and the wristband 2 is attached on a wrist of the patient A.

For example, the sensor 3a for measuring an electrocardiogram is attached on the patient A by the medical worker. The patient A is, for example, lying on a bed 61 in the hospital room 100. The start switch 23 for activating the human body communication unit 22 of the wristband 2 is pressed by the medical worker. On this occasion, it is desirable that the medical worker visually confirms the patient's name inscribed on the wristband 2, and confirms that the patient A is the patient herself.

The human body communication unit 22 of the wristband 2 starts human body communication so that the patient ID of the patient A stored in the storage unit 21 can be transmitted to the sensor 3a through the body surface of the patient A. The patient ID is then automatically transmitted from the wristband 2 to the sensor 3a every fixed period.

The human body communication unit 31 of the sensor 3a acquires the patient ID transmitted from the wristband 2. In this case, the sensor 3a acquires the patient ID from the wristband 2 before starting measuring an electrocardiogram. Therefore, for example, before the sensor 3a acquires the patient ID, the sensor 3a may be configured to stop measuring the electrocardiogram by the measurement unit 32.

Incidentally, the communication method between the wristband 2 and the sensor 3a may be bidirectional communication or unidirectional communication. For example, in the case of the bidirectional communication, the sensor 3a may be configured to transmit a signal for requesting the patient ID to the wristband 2, and acquire the patient ID from the wristband 2. In addition, although not shown, the sensor 3a may be configured to have a storage unit so that the patient ID acquired from the wristband 2 can be stored in the storage unit.

In the sensor 3a, the patient ID of the patient A is associated with the electrocardiogram of the patient A measured by the measurement unit 32, and the electrocardiogram including the patient ID is then transmitted from the transmission unit 33 to the bedside monitor 4 by wireless. The sensor 3a writes the patient ID, for example, into a header area, and then transmits the patient ID-including electrocardiogram in which electrocardiogram data are written into a data region following the latter part of the header area.

In the sensor 3a, the transmission unit 33 does not start transmitting the electrocardiogram when the measurement unit 32 starts measuring the electrocardiogram before the patient ID is acquired from the wristband 2. That is, the sensor 3a is set so that the electrocardiogram associated with no patient ID can be prevented from being transmitted from the transmission unit 33 to the bedside monitor 4.

Upon reception of the electrocardiogram including the patient ID, the bedside monitor 4 refers to the patient information table held by the nurse call system 5 of the nurse station 200 to specify the name ("Ms. A") of the patient A associated with the patient ID. The bedside monitor 4 displays a message indicating "Ms. A's electrocardiogram has been received", as a pop-up screen 42 on the display screen 41, for example, as shown in FIG. 3.

The medical worker confirms display contents of the pop-up screen 42 and confirms that Ms. A is the patient herself. Then, medical worker touches the pop-up screen 42.

In the bedside monitor 4, the pop-up screen 42 is cancelled, and the electrocardiogram waveform of the patient A, for example, together with the name ("Ms. A") of the patient A, is displayed on the display screen 41, as shown in FIG.

4. Incidentally, although the case of the sensor 3a for measuring an electrocardiogram has been described in the example, the sensor 3b for measuring body temperature or the sensor 3c for measuring respiration can also operate similarly so that each vital information can be displayed on the display screen 41.

Each vital information of the patient A displayed on the aforementioned bedside monitor 4 can be transmitted from the bedside monitor 4 to the nurse call system 5 by wireless by an operation on the nurse call system 5, and displayed on the display screen 51 of the nurse call system 5.

In a background-art medical device for measuring patient information using wireless sensors, for example, assume that sensors a to c (not shown) are attached on a patient A and sensors d to f (not shown) are attached on a patient B. In this case, the medical device which has received information from the sensors cannot automatically associate information of the sensor a with information of the patient A. In this case, for example, device numbers belonging to the sensors and pieces of information about the patients can be associated with each other respectively. There is however a possibility that a human error may occur in the association work. In addition, for example, it may be also considered that a patient ID can be manually inputted in accordance with each sensor and associated therewith. Similarly to the aforementioned case, there is however a possibility that a human error may occur. In addition, whenever the patient is replaced by another person, work for deleting the associated patient ID is necessary to thereby result in an increase in workload.

To solve the problems, according to the sensor system 1 according to the embodiment, the unique patient ID given to the patent A by the medical worker is transmitted from the wristband 2 to the sensor 3a through the body surface of the patient A. Therefore, the sensor 3a can accurately associate the patient ID of the patient A on which the sensor 3a is attached, with the electrocardiogram measured by the sensor 3a. A signal of the electrocardiogram including the patient ID can be received by the bedside monitor 4 in a state in which the measured electrocardiogram and the patient ID are associated with each other accurately. Accordingly, the signal of the electrocardiogram including the patient ID can be displayed on the display screen 41 of the bedside monitor 4 in the state in which the sensor 3a measuring the electrocardiogram and the patient A ("Ms. A") are associated with each other accurately.

In addition, the wristband 2 is wearable on the wrist of the patient A. The name of the patient A is inscribed on the wristband 2. Therefore, the patient ID of the patient A stored by the wristband 2 can be given to the sensor 3a surely through the body surface of the patient A. In addition, when the medical worker attaches the sensor 3a on the patient A, the medical worker can visually confirm that the name of the patient A on the wristband 2 and the patient herself are associated with each other accurately. Incidentally, here, "inscribe" means that, for example, the wristband 2 may have a liquid crystal screen and also provide a mode in which the name of the patient can be displayed on the liquid crystal screen in accordance with a button operation etc.

In addition, the sensor 3a has a configuration to acquire the patient ID from the wristband 2 before starting measuring the electrocardiogram. In addition, the sensor 3a has the following configuration. That is, when the sensor 3a starts measuring the electrocardiogram before acquiring the patient ID, the sensor 3a does not start transmitting the electrocardiogram to the bedside monitor 4. Therefore, the medical worker or the patient does not do any special work for associating the sensor with the patient but the patient ID of the patient A on which the sensor 3a is attached can be automatically associated with the electrocardiogram. In addition, it is possible to suppress occurrence of a situation in which the electrocardiogram measured by the sensor 3a and the patient A cannot be associated with each other accurately.

<Modification>

Assume that measurement of an electrocardiogram is started by a measurement unit 32 of a sensor 3a before a patient ID is acquired by the sensor 3a from a wristband 2. In this case, the sensor 3a may associate an identifier (e.g. a non-giving identifier) with the electrocardiogram and transmit the electrocardiogram including the non-giving identifier from a transmission unit 33 to a bedside monitor 4. The non-giving identifier indicates that the patient ID has not been associated yet. In this case, the bedside monitor 4 which has received the electrocardiogram including the non-giving identifier may display, for example, a message indicating that "the patient has not been specified yet" on a display screen 41.

According to such a configuration, it is possible to suppress occurrence of a situation in which an electrocardiogram measured by the sensor 3a and a patient A cannot be associated with each other accurately. Similarly to the aforementioned embodiment, the electrocardiogram of the patient A measured by the sensor 3a attached on the patient A can be displayed on the display screen 41 of the bedside monitor 4 etc. In addition, when, for example, there arises a problem that a patient ID is not written into a storage unit 21 of a wristband 2 attached by the patient A, the problem can be detected.

Incidentally, the invention is not limited to the aforementioned embodiment. Any modification, improvement, etc. can be made on the invention desirably and suitably. Besides, the materials, shapes, dimensions, numerical values, forms, numbers, arrangement places etc. of the respective constituent elements in the aforementioned embodiment are not limited but may be set desirably as long as the invention can be achieved.

The present application is based on Japanese Patent Application No. 2016-127894 filed on Jun. 28, 2016, the contents of which are hereby incorporated by reference.

1: sensor system, 2: wristband (example of ID tag), 3 (3a to 3c): sensor, 4: bedside monitor (example of external device), 5: nurse call system, 21: storage unit, 22, 31: human body communication unit, 23: start switch, 24, 34: power supply unit, 32: measurement unit, 33: transmission unit, 41, 51: display screen, 100: hospital room, 200: nurse station.

What is claimed is:

1. A sensor system comprising:
   an ID tag which has a storage unit storing patient identification information so that a patient can be identified by the patient identification information; and
   a sensor including a wireless communication unit to communicate with an external device, the sensor configured to measure vital information of the patient,
   wherein:
      the ID tag transmits the patient identification information to the sensor by human body communication through a surface of a body of the patient in a state in which the ID tag and the sensor are attached to the patient,
      the sensor receives the patient identification information from the ID tag and associates the received patient identification information with the vital information and then transmits, by the wireless communication unit, the vital information associated with the patient identification information to the external device, and when the sensor starts to measure the vital information before acquiring the patient identification information, the sensor is further configured to associate a non-giving identifier with the vital information and to transmit the vital information including the non-giving identifier to the external device, the non-giving identifier indicating that the patient identification information has not been associated yet, and a monitor configured to:

display the measured vital information with the patient identification information when the vital information is associated with the patient identification information; and display the measured vital information without the patient identification information when the vital information is associated with the non-giving identifier, wherein the monitor is configured to, when the vital information is associated with the non-giving identifier, display the measured vital information with a message indicating that the patient has not been identified yet.

2. The sensor system according to claim 1, wherein:
the ID tag can be attached on a part of the body of the patient.

3. The sensor system according to claim 2, wherein:
the ID tag is a wristband which is wearable on a wrist of the patient, and the patient identification information of the patient is described on the wristband.

4. The sensor system according to claim 1, wherein:
the sensor acquires the patient identification information from the ID tag before starting measuring the vital information.

5. The sensor system according to claim 1, wherein:
when the sensor starts measuring the vital information before acquiring the patient identification information, the sensor does not start transmitting the vital information to the external device.

6. The sensor system according to claim 1, wherein:
the sensor directly transmits the vital information including the patient identification information to the external device.

* * * * *